United States Patent [19]

Tompkins

[11] 4,030,498

[45] June 21, 1977

[54] SYRINGE

[75] Inventor: Douglas L. Tompkins, Northbrook, Ill.

[73] Assignee: Baxter Travenol Laboratories, Inc., Deerfield, Ill.

[22] Filed: July 22, 1976

[21] Appl. No.: 707,684

Related U.S. Application Data

[63] Continuation of Ser. No. 517,998, Oct. 25, 1974, abandoned.

[52] U.S. Cl. .............................. 128/218 P; 128/234
[51] Int. Cl.² .......................................... A61M 5/00
[58] Field of Search ..... 128/218 P, 218 R, 218 PA, 128/218 M, 215, 216, 234

[56] References Cited

UNITED STATES PATENTS

| 766,121 | 7/1904 | Stearns | 128/218 P |
|---|---|---|---|
| 786,697 | 4/1905 | Wackenhuth | 128/218 P |
| 788,059 | 4/1905 | McElroy | 128/234 |
| 1,771,219 | 7/1930 | Hein | 128/218 P |
| 2,688,325 | 9/1954 | Lockhart | 128/218 P |
| 2,771,880 | 11/1956 | Gotthart | 128/218 P |
| 2,842,127 | 7/1958 | Everett | 128/218 P |
| 2,896,621 | 7/1959 | Rodrigues | 128/DIG. 1 |
| 2,902,035 | 9/1959 | Hartley | 128/218 P |
| 3,255,752 | 6/1966 | Dick | 128/218 M |

FOREIGN PATENTS OR APPLICATIONS

| 325,274 | 4/1903 | France | 128/218 P |
|---|---|---|---|
| 67,033 | 2/1893 | Germany | 128/218 P |

*Primary Examiner*—John D. Yasko
*Attorney, Agent, or Firm*—George H. Gerstman; Paul C. Flattery

[57] ABSTRACT

A contamination resistant syringe is provided in which two sealing rings are axially spaced from each other. The sealing rings are prevented from sweeping the same area and there is no communication between the chamber defined by the two sealing rings and the discharge area forward of the inner sealing ring. In this manner, contamination which might enter from the rear of the barrel will be prevented from contact with the inner ssealing ring.

7 Claims, 7 Drawing Figures

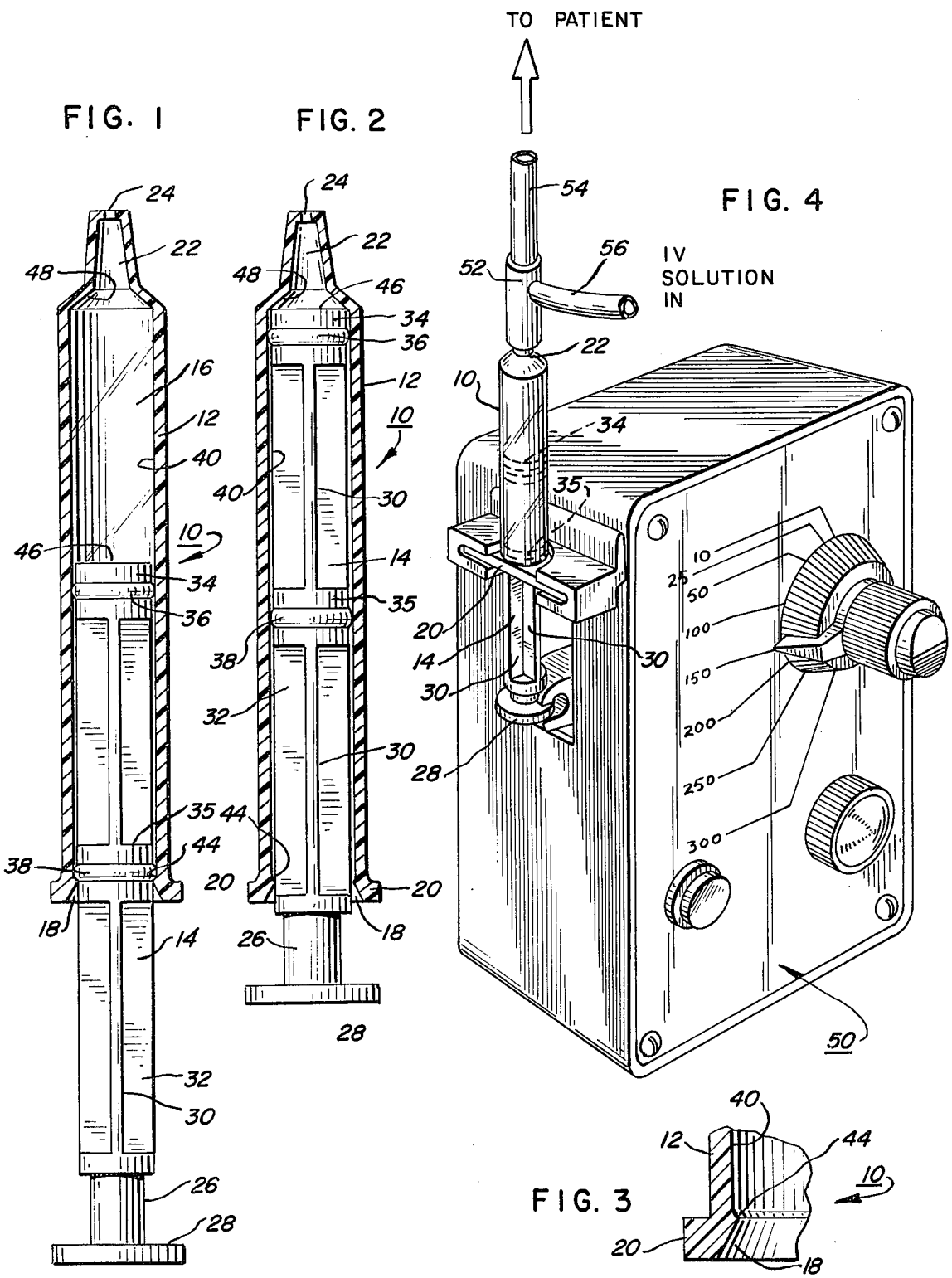

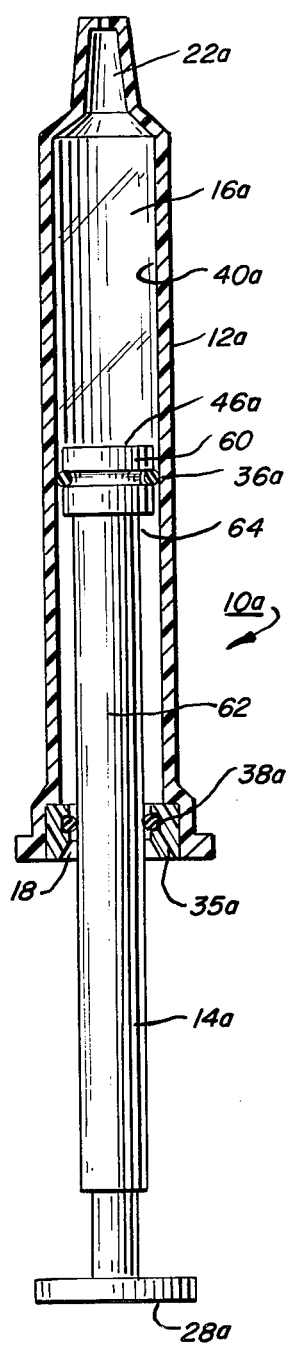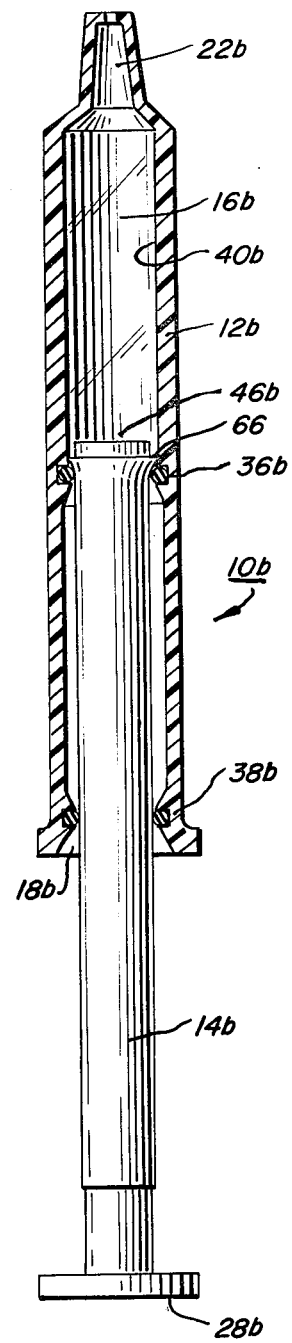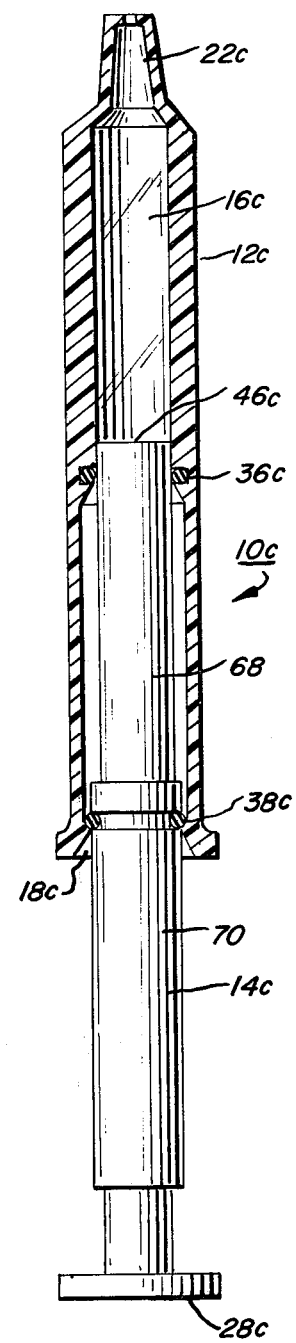

SYRINGE

This is a continuation of application Ser. No. 517,998, filed Oct. 25, 1974, now abandoned.

BACKGROUND OF THE INVENTION

This invention relates to an improved hypodermic syringe.

A typical syringe includes a barrel having a discharge orifice at its front end and defining a bore through which a plunger extends and travels. The plunger typically carries a piston which sweeps a portion of the bore so as to draw in fluid on the intake stroke (pullback of the plunger) and to discharge fluid on the discharge stroke (push-in of the plunger). Many syringes are pre-filled and no intake stroke is required by the operator.

Although syringes are generally packaged in a sterile manner, once the syringe is removed from its package contamination of the bore may occur. Typically such contamination might occur by contaminants entering the bore from the rear thereof. During the intake stroke, the piston ring may communicate with the contaminant and on the discharge stroke, the contaminant may be brought forward by the piston ring and communicated with the fluid medicament being discharged.

It is, therefore, an object of the present invention, to provide a syringe having means to prevent fluid medicament from communicating with the rearward, possibly contaminated portion of the syringe's barrel.

A further object of the present invention is to provide a syringe that is simple in construction and efficient to manufacture.

Another object of the present invention is to provide a syringe having a pair of axially spaced pistons with the chamber defined by the pistons being prevented from communicating with the area forward of the forward piston.

A further object of the present invention is to provide a syringe that is usable with an infusion pump, that is simple in construction and has means for effectively segregating the front portion of the bore from the rear portion thereof.

Other objects and advantages of the present invention will become apparent as the description proceeds.

SUMMARY OF THE INVENTION

In accordance with the present invention, there is provided a syringe comprising a barrel defining a bore and having a discharge portion, and a plunger extending into the bore and movable therewithin. The improvement comprises inner sealing means within the bore and outer sealing means within the bore. The inner and outer sealing means are spaced axially from each other and are constructed and positioned for preventing communication between (1) the chamber defined by the inner and outer sealing means, and (2) the area forward of the inner sealing means.

In one embodiment of the invention, the inner and outer sealing means are carried by the plunger and the outer sealing means is prevented from moving into the area in which the inner sealing means travels. In this embodiment, the barrel includes a smooth continuous wall portion defining the bore in which the inner sealing means travels. Thus a constant seal is provided by the inner sealing means along the wall portion.

In a modified form of the invention, inner sealing means is carried by the plunger and the outer sealing means is fixed to the barrel. In another form of the invention, both inner and outer sealing means are fixed to the barrel and in another form of the invention, the inner sealing means is fixed to the barrel and the outer sealing means is carried by the plunger.

In all of the forms of the present invention, communication is prevented between the chamber defined by the inner and outer sealing means and the area forward of the inner sealing means.

A more detailed explanation of the invention is provided in the following description and claims, and is illustrated in the accompanying drawings.

BRIEF DESCRIPTION OF THE DRAWING

FIG. 1 is an elevational view of a syringe constructed in accordance with the principles of the present invention with the plunger in its fully extended position;

FIG. 2 is an elevational view thereof with the plunger in its fully inserted position;

FIG. 3 is a fragmentary enlarged view of a portion of the syringe of FIGS. 1 and 2;

FIG. 4 is a perspective view of the syringe of FIGS. 1-3 coupled to an infusion pump;

FIG. 5 is an elevational view of a syringe constructed in accordance with a modified form of the invention;

FIG. 6 is an elevational view of a syringe construced in accordance with another modified form of the invention; and FIG. 7 is an elevational view of a syringe constructed in accordance with a further modified form of the present invention.

BRIEF DESCRIPTION OF THE ILLUSTRATIVE EMBODIMENT

Referring to the drawings, a syringe 10 is shown therein comprising a barrel 12 and a plunger 14. Barrel 12 defines a bore 16 and has a rear entrance 18 with an outstanding flange 20. The front of the bore communicates with a discharge portion 22 having a discharge orifice 24.

The plunger 14 comprises a rod 26 having an end knob 28 and a number of longitudinal ribs 30 which define longitudinal grooves 32. A pair of axially spaced sealing means 34, 35, comprising inner piston 34 and outer piston 35 are fastened to the plunger 14. Inner piston 34 carries a rubber O-ring 36 and outer piston 35 also carries a rubber O-ring 38, which O-rings are compressed to sweep the wall 40 defining the bore 16 tightly.

The wall 40 defining the bore 16 is smooth and continuous so as to provide a continual seal by both O-rings 36, 38 throughout their travel. The O-rings are axially spaced from each other more than one-half the functional length of the bore 16 so that the swept area of each O-ring will not overlie the swept area of the other O-ring will not overlies the swept area of the other O-ring.

In addition, a detent 44 is provided at the end of the barrel 12 to cooperatively limit movement of the plunger 14 within the barrel 12. The detent 44 comprises an annular ring having an inner diameter that is slightly smaller than the outer diameter of the O-rings. However, the inner diameter of annular ring 44 is greater than the external diameter of the pistons 34, 35 (without O-rings) and thus permits the resilient O-rings to be forced past annular ring 44 if enough force is used to compress the O-rings significantly. This permits plunger 14 to be forced in barrel 12 during assembly, but limits rearward movement thereof. Forward movement of the plunger is limited because the leading end 46 of piston 34 will abut wall 48.

By constructing the syringe 10 as aforesaid, it can be seen that there is no overlap in the swept areas of the two O-rings 36, 38. This prevents contamination of inner O-ring 36 during use of the syringe, because contaminant entering the bore 16 from the rear thereof can communicate only with the outer O-ring 38 and communication between the outer O-ring 38 and the inner O-ring 36 is prevented.

Referring to FIG. 4, it is seen that syringe 10 is coupled to an infusion pump 50. The infusion pump 50 has a limited stroke, thus further preventing overlap of the areas swept by the respective O-rings. An infusion pump which could be used with the syringe of the present invention, and which has a variable delivery rate, is disclosed in U.S. patent application Ser. No. 440,410, filed Feb. 17, 1974 in the name of Raymond G. Olson and assigned to the assignee of the present invention.

Syringe 10 has a valve arrangement 52 connected to the discharge portion 22 of the syringe and coupled to outlet tubing 54. The valve arrangement 52 is preferably a pair of one-way valves permitting flow only from an IV bottle to the syringe via the inlet 56 and from the syringe to the patient-connected outlet tubing 54.

In FIGS. 5–7, three modified forms of the invention are shown. The reference numerals used in these Figures are similar to those used in FIGS. 1 and 2 for similar structure, but the letters a, b and c have been added after the numeral in FIGS. 6, 7 and 8, respectively.

Referring to FIG. 5, syringe 10a illustrated therein includes a barrel 12a having a bore 16a defined by a smooth continuous inner wall 48. Plunger 14a extending into bore 16a carries O-ring 36a adjacent its forward end 46a. Adjacent rear entrance 18a of barrel 12a, there is connected sealing means 35a including O-ring 38a.

In constructing the syringe assembly, sealing means 35a is inserted into the barrel 12a from the rear thereof, after the main portions of the plunger 14a have been inserted into the barrel and before knob 28a is attached to the main portions of the plunger 14a.

Plunger 14a has an enlarged forward portion 60 to which O-ring 36a is connected. Rear portion 62 of plunger 14a has a smaller diameter than forward portion 60 and O-ring 38a, which is carried by sealing means 35a, is constructed so as to wipe the surface of rear portion 62 while O-ring 36a wipes wall 40a.

The rearward stroke of plunger 14a is limited by abutment wall 64 which prevents forward portion 60 from being wiped by O-ring 38a. In this manner, material cannot be transferred from O-ring 38a to O-ring 36a.

Referring to FIG. 6, barrel 12b of syringe 10b carries inner O-ring 36b which is axially spaced from outer O-ring 38b. Both O-rings are connected to inside wall 40b which defines bore 16b. A detent 66 is formed at the front end of plunger 14b to prevent the plunger from being withdrawn more than a predetermined amount. The outer diameter of detent 66 is slightly greater than the inner diameter of O-ring 36b so that when the plunger 14b is withdrawn, its front end will not pass O-ring 36b. However, in assembliing the syringe assembly, the detent 66 can be forced past O-ring 36b.

It can be seen that utilizing the construction shown in FIG. 6, contaminants carried by O-ring 38b cannot be transferred to O-ring 36b, as O-rings 36b and 38b will always wipe different portions of plunger 14b.

Referring to FIG. 7, inner O-ring 36c is attached to barrel 12c and an outer O-ring 38c is carried by plunger 14c. Forward portion 68 of plunger 14c has a smaller diameter than rearward portion 70 thereof, so as to provide an abutment wall 72. The external diameter of portion 70 is slightly greater than the internal diameter of O-ring 36c. Thus, during the forward stroke of plunger 14c, abutment wall 72 will engage O-ring 36c thereby preventing O-rings 36c and 38c from wiping the same area. In this manner, contaminant material will be prevented from being transferred from O-ring 38c to O-ring 36c.

It is seen that a novel syringe has been provided, which is simple in construction and which effectively segregates the forward discharge portion of the barrel from the rear portion thereof. Although one application of the present invention is with a mechanical infusion device, such as illustrated in FIG. 4, the syringe of the present invention could also be used in other environments. For example, the syringe could contain potentially hazardous substances (such as biologically or radioactively potent materials) and prevent contamination of the syringe user or the surroundings. Thus the device of the present invention is applicable to sampling and transferring functions in addition to hypodermic or infusion uses.

Although illustrative embodiments of the invention have been shown and described, it is to be understood that various modifications and substitutions may be made by those skilled in the art without departing from the novel spirit and scope of the present invention.

What is claimed is:

1. In a syringe comprising a barrel defining a bore and having a discharge portion, and a plunger extending into said bore and movable therewithin, the improvement comprising, in combination: inner sealing means carried by said plunger and movable axially within said bore in an area proximate to said discharge portion for substantially preventing leakage of medicament or other biologic fluid contained in the space forward of said inner sealing means adjacent said discharge portion; outer sealing means carried by said plunger, said outer sealing means being spaced axially from said inner sealing means and movable axially within said bore in an area behind the travel area of said inner sealing means; said plunger having an axial length within the bore of more than one-half of the functional length of the bore void of sealing rings; and means for preventing said outer sealing means from moving in the area in which said inner sealing means travels.

2. In a syringe as described in claim 1, said inner and outer sealing means including O-rings.

3. In a syringe as described in claim 1, said means for preventing said outer sealing means from moving in the area in which said inner sealing means travels comprising an infusion pump coupled to said syringe and having a limited stroke, whereby said plunger travel is limited by said stroke.

4. In a syringe as described in claim 1, said means for preventing said outer sealing means from moving in the area in which said inner sealing means travels comprising said inner and outer sealing means being axially spaced from each other more than one-half the functional length of said bore.

5. In a syringe as described in claim 1, said means for preventing said outer sealing means from moving in the area in which said sealing means travels comprising a detent carried by said barrel to limit movement of said plunger within said barrel.

6. In a syringe as described in claim 1, including a detent carried by said barrel to limit movement of said plunger within said barrel.

7. In a syringe as described in claim 6, wherein said detent comprises an annular ring having an inner diameter that is greater than the outer diameter of said sealing rings.

* * * * *